United States Patent
Roorda et al.

(10) Patent No.: US 9,486,230 B2
(45) Date of Patent: *Nov. 8, 2016

(54) PERCUTANEOUS ANEURYSM INVERSION AND LIGATION

(71) Applicant: Abbott Cardiovascular Systems Inc., Santa Clara, CA (US)

(72) Inventors: Wouter E. Roorda, Palo Alto, CA (US); Randolf von Oepen, Aptos, CA (US); Travis Richard Yribarren, Coarsegold, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 76 days.

This patent is subject to a terminal disclaimer.

(21) Appl. No.: 14/221,153

(22) Filed: Mar. 20, 2014

(65) Prior Publication Data

US 2014/0207157 A1 Jul. 24, 2014

Related U.S. Application Data

(63) Continuation of application No. 13/186,229, filed on Jul. 19, 2011, now Pat. No. 8,728,094.

(51) Int. Cl.
| | |
|---|---|
| *A61B 17/10* | (2006.01) |
| *A61B 17/22* | (2006.01) |
| *A61B 17/04* | (2006.01) |
| *A61B 17/12* | (2006.01) |

(52) U.S. Cl.
CPC .......... *A61B 17/22* (2013.01); *A61B 17/0401* (2013.01); *A61B 17/12013* (2013.01); *A61B 17/12113* (2013.01); *A61B 2017/0414* (2013.01); *A61B 2017/0464* (2013.01); *A61B 2017/0496* (2013.01)

(58) Field of Classification Search
CPC ................... A61B 17/0401; A61B 17/12013; A61B 17/12113; A61B 17/22; A61B 2017/0414; A61B 2017/0464; A61B 2017/0496
See application file for complete search history.

(56) References Cited

U.S. PATENT DOCUMENTS

| | | | |
|---|---|---|---|
| 4,340,061 A | 7/1982 | Kees et al. | |
| 4,735,194 A | 4/1988 | Stiegmann | |
| 5,284,488 A | 2/1994 | Sideris | |
| 5,484,451 A | 1/1996 | Akopov et al. | |
| 5,921,993 A | 7/1999 | Yoon | |
| 7,566,336 B2 | 7/2009 | Corcoran et al. | |
| 8,062,308 B2 | 11/2011 | Noda et al. | |
| 2003/0158563 A1* | 8/2003 | McClellan | A61B 17/12009 606/151 |
| 2007/0225734 A1 | 9/2007 | Bell et al. | |
| 2008/0312664 A1 | 12/2008 | Bardsley et al. | |

FOREIGN PATENT DOCUMENTS

WO  WO 2006068981  6/2006

OTHER PUBLICATIONS

Strollberger, Claudia, et al. "Elimination of the Left Atrial Appendage to Prevent Stroke or Embolism?: Anatomic, Physiologic, and Pathophysiologic Considerations", Downloaded from chestjournal.chestpubs.org by guest on Jun. 28, 2010; copyright 2003 American College of Chest Physicians, (2003).

* cited by examiner

*Primary Examiner* — Gregory Anderson
(74) *Attorney, Agent, or Firm* — Randy Shen; Blakely, Sokoloff, Taylor & Zafman LLP

(57) ABSTRACT

Devices and methods for percutaneously treating and removing aneurysms or other anomalous tissue associated with vascular, intestinal, or other body tissue.

17 Claims, 6 Drawing Sheets

PERCUTANEOUS ANEURYSM INVERSION AND LIGATION

RELATED APPLICATIONS

Applicant claims the benefit of priority of prior, co-pending U.S. application Ser. No. 13/186,229, filed Jul. 19, 2011, the entirety of which is incorporated herein by reference.

BACKGROUND

In many different diseases or problems caused by anatomical anomalies, an extraneous or diseased piece of tissue is connected to normal tissue. In some cases this connection contains an ostium such as the opening between a vessel wall and an aneurysm or the opening between the large intestine and the appendix. One method of treating such problems is to seal or close the ostium and remove the extraneous tissue. Practitioners usually accomplish this type of intervention surgically or laparoscopically. But vascular or intestinal access in some cases results in less invasive treatment. This invention relates to procedures and devices to treat abnormal tissue by surgically intervening using vascular or intestinal access to the tissue.

SUMMARY

As in one inventive embodiment, one way of employing vascular access or access through another body lumen is to track the surgical device within the lumen until the device reaches the treatment location. Thus, the device would be located inside the lumen, near the ostium to the diseased or anomalous tissue, with the tissue being distal to the ostium.

The treatment method includes steps of inverting the diseased or anomalous tissue into the body lumen, closing the ostium, and resecting or cutting the diseased or anomalous tissue from the body and removing the tissue from the body through the lumen.

In some embodiments, including embodiments to treat diseased tissue that is separated from normal tissue by something more like a region and less like an ostium, an artificial ostium is first created, for example by retracting the tissue. Once the artificial ostium has been formed, diseased or anomalous tissue is inverted through it as before.

DETAILED DESCRIPTION

Figure 1:
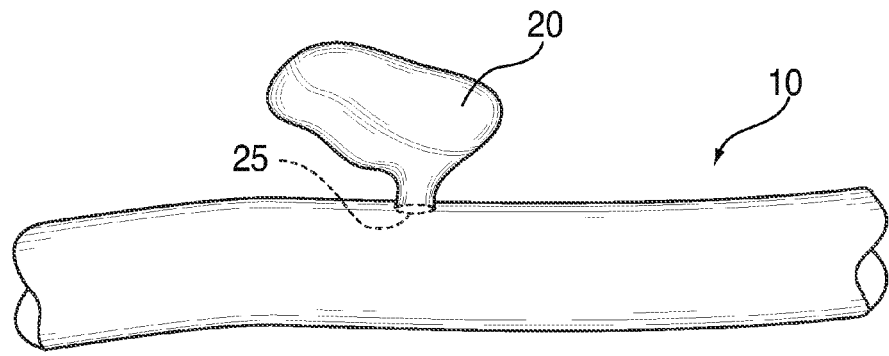
FIG. 1 is a representation of a vessel with an aneurysm.

A view of a vessel that has anomalous tissue, specifically an aneurysm, is shown in FIG. 1. Vessel 10, aneurysm 20, and ostium 25 connecting vessel 10 and aneurysm 20 are shown. Aneurysm 20 has a substantially larger diameter than ostium 25 in this figure.

Figure 2:
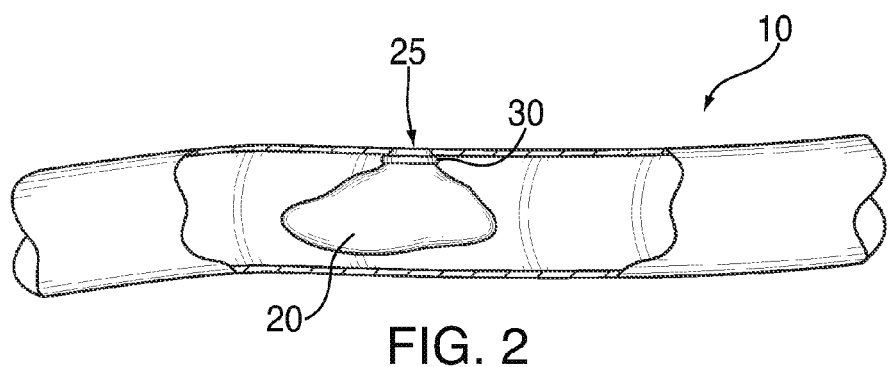
FIG. 2 is a representation of a cross-section of a vessel showing a ligature placed around the connection between the vessel and the aneurysm after ligation of the aneurysm.
Figure 3:
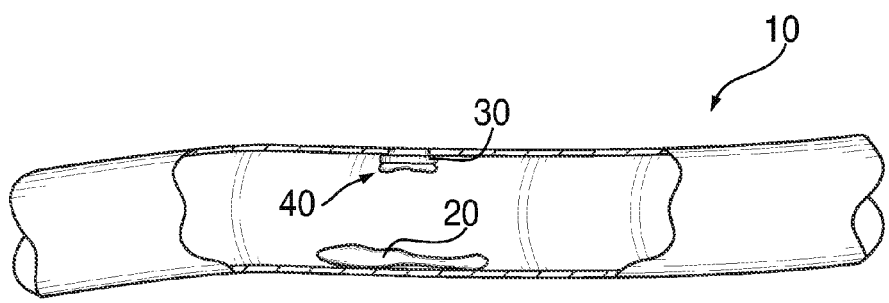
FIG. 3 is a representation of the cross-section of the vessel of FIG. 2 depicting the resection of the aneurytic tissue.

FIG. 2 depicts a step in treating an aneurysm. Aneurysm 20 has been inverted into vessel 10 through ostium 25 and ligature 30. Some embodiments employ ligation before inversion, employ ligation after inversion, or employ no ligation at all. After inversion, as shown in FIG. 3, the excess tissue is resected. This resection is indicated as 40 in the figure.

Figure 4:
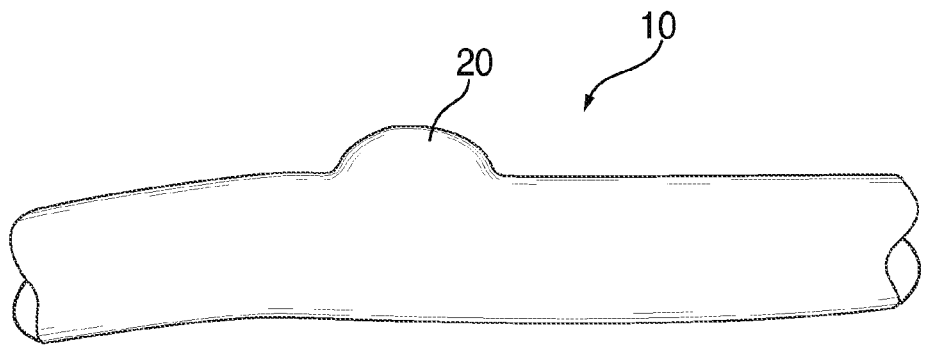
FIG. 4 is a representation of a vessel and an aneurysm in which the ostium or opening into the aneurysm is comparable to the diameter of the aneurysm.

In FIG. 4, aneurysm 20 has a slightly different presentation. As depicted, an ostium sits between aneurysm 20 and vessel 10. But in this presentation, it is more like a transition region between the vessel and the aneurysm and less like a clearly demarked region. The diameter of aneurysm 20 more closely matches the diameter of the ostium when it presents in this way. In essence, this means that the anomalous tissue may be less susceptible to inversion through the ostium because the ostium is much less well-defined and less localized making it less capable of serving as an inversion region.

Figure 5:
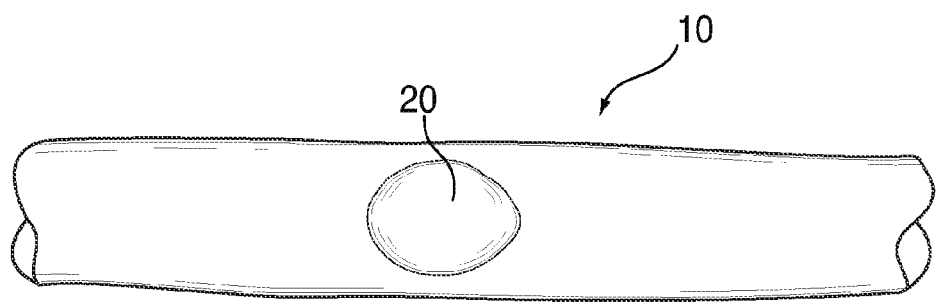
FIG. 5 is a top view of the vessel and aneurysm of FIG. 4.

FIG. 5 shows the aneurysm of FIG. 4 viewed perpendicularly to an axis of ostium 25 and substantially radially from the vessel 10. A closer match between the diameter of the anomalous tissue (such as aneurysm 20) and the diameter of the ostium may call for a different type of ligature 30 or additional steps in ligating the tissue.

Figure 6:
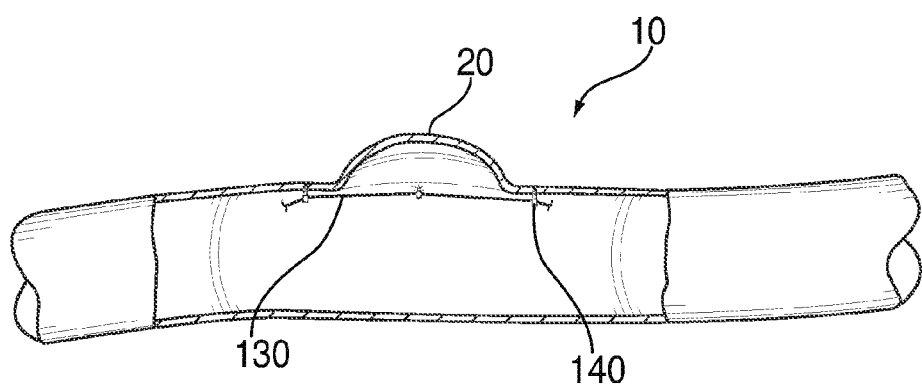
FIG. 6 is a representation of the cross-section of a vessel with an aneurysm with a side-view of an installed ligature.

FIG. 6 depicts a side view of such a different ligature type. Once again, the figure depicts vessel 10, aneurysm 20, and the less pronounced ostium. The ligature in this case is labeled 130. Ligature 130 comprises one or more semi-flexible filaments, cords, or wires that are disposed around or through tissue attaching moieties; more specifically in some embodiments, the filaments, cords, or wires of ligature 130 are disposed around or through anchors 140. Anchors 140 connect into the tissue surrounding the ostium. In some embodiments, these semi-flexible filaments, cords, or wires act as a drawstring. Anchors 140 can be eyelets, in which case the drawstring passes through anchors 140. Alternatively, anchors 140 can be posts or hooks, in which case the drawstring is disposed around anchors 140.

Figure 7:
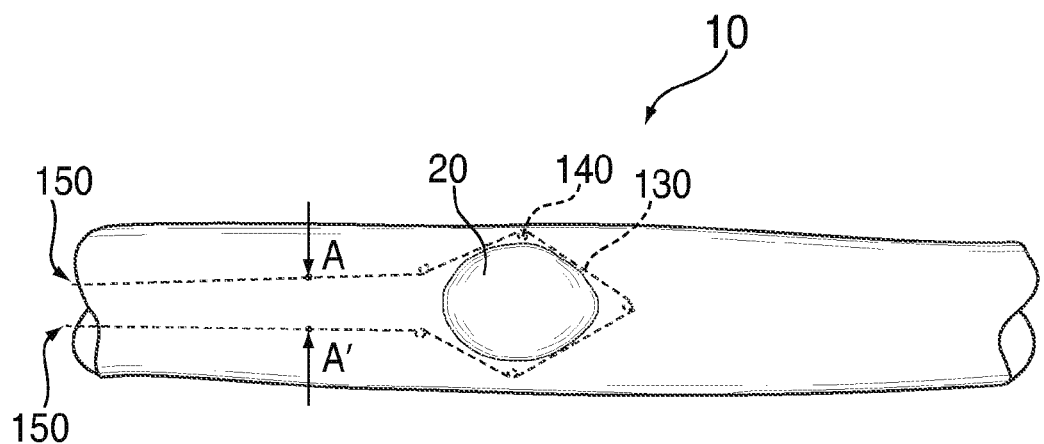
FIG. 7 is a representation of the aneurysm, with the ligature installed, looking down on the aneurysm.

FIG. 7 depicts an alternative view of FIG. 4 along the axis perpendicular to ostium 25. Ligature 130 laces through anchors 140 and has two ends 150 before ligature 130 is tied off. Positions A and A' are shown as a reference.

Figure 8:
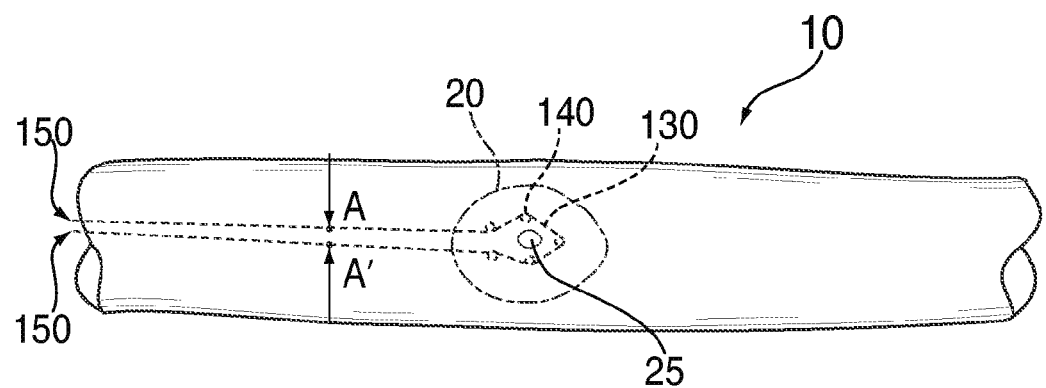
FIG. 8 is a representation of the vessel with a ligated aneurysm looking down on the aneurysm.

FIG. 8 shows a similar view to that shown in FIG. 7, except in FIG. 8, ligature 130 has been tightened by extending ends 150. The positions A and A' are further away from adjacent anchors 140. This motion tightens the ligature and pulls anchors 140 closer together, causing the less pronounced ostium to effectively decrease in diameter and form a more defined ostium 25. In operation, ends 150 are tied to secure ligature 130.

After ends 150 are tied, the anomalous tissue or aneurytic tissue 20 is inverted through ostium 25 and then resected and removed from vessel 10.

Those of ordinary skill in the art will recognize other functionally equivalent anchors all of which are within the scope of this invention. These anchor examples refer to anchors that are used sometimes in mitral valve repair.

An anchor example that is useful in some embodiments of this invention is a curved nitinol wire that can be straightened within a catheter lumen, e.g. a needle catheter lumen. When the wire is deployed from the lumen, it engages the tissue and springs back to its curved form. In this way, it also grasps the tissue and creates a circular anchor within the tissue. A suture may be passed through this anchor to assist ligation.

Another form of anchor 140 that may be useful in some embodiments of this invention includes a simple, barbed needle that can be deployed into the tissue. The barb instills a one-way motion capability, i.e. it punctures into tissue, but the barb resists the withdrawal of anchor 140. Furthermore, anchor embodiments that can be screwed into tissue may be used. In this case, the anchor may have a screw-type thread along its outer surface that engages the tissue when the anchor is deployed.

Another tissue anchor embodiment uses percutaneous placement of sutures with tissue anchors 140. Such anchors 140 can be positioned at appropriate positions around the ostium to aneurysm 20 using a needle catheter, for example. The position of the tissue anchors 140 will depend on the size of the aneurysm 20 and the width of the ostium. Once the sutures are anchored, they can be cinched together by a locking device at the tip of a catheter. In some embodiments, operation of the locking device advances it for over the sutures until it reaches the aneurysm 20. The locking device can be a nitinol clip that is released from the tip of the catheter and captures the sutures or a twist- or compression-type of cleat that clamps the sutures. Once the sutures are secured, they may be trimmed by a cutting device at the tip of the catheter.

Figure 9:
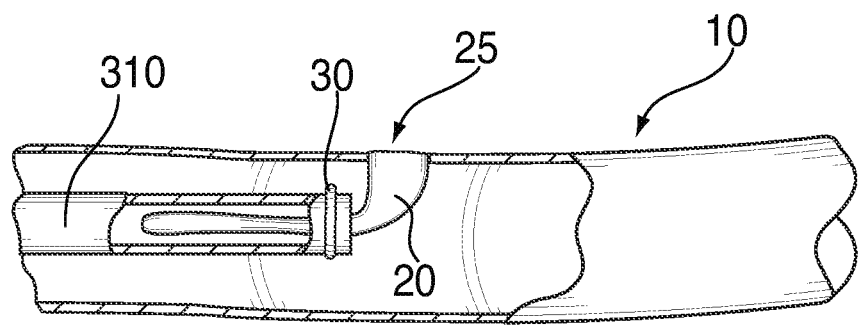
FIG. 9 is a representation of the cross-section of a vessel with an aneurysm in which the aneurysm has been retracted into a catheter.

FIG. 9 shows vessel 10 in partial cross-section. Aneurytic tissue 20 is shown inverted through ostium 25. Retracting aneurytic tissue 20 into the tubular portion of device 310 accomplishes this inversion. In FIG. 9, device 310 uses suction in its tubular portion to hold and pull aneurytic tissue 20 into device 310. Ligature 30 is situated on or near the end of device 310 awaiting deployment.

Figure 10:
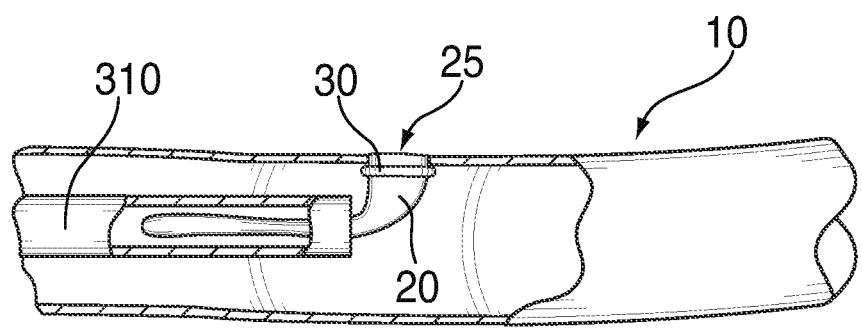
FIG. 10 is a representation of the cross-section of a vessel with an aneurysm in which the aneurysm has been retracted into a catheter after the ligature has been applied.

FIG. 10 depicts ligature 30 after deployment and after retraction of aneurytic tissue 20. Once ligature 30 has been deployed, aneurytic tissue 20 can be resected and removed from vessel 10.

Figure 11:
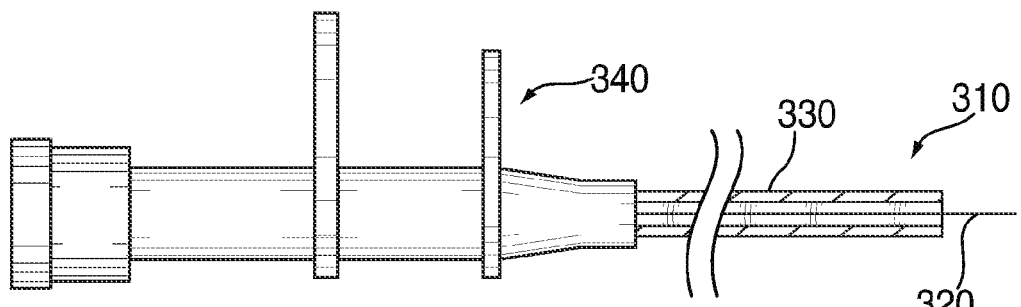
FIG. 11 is a representation of a partial cross-section of a device.

FIG. 11 shows an embodiment of device 310. In some embodiments, device 310 comprises an elongate structure extending between proximal and distal ends. A handle 340 is disposed near the proximal end of device 310. The elongate structure is catheter-like in nature and serves to couple the handle 340 to pieces at the distal end of device 310 in a manner that facilitates manipulating those distal end pieces from the handle 340. Thus, device 310 allows for percutaneous treatment of a tissue anomaly within a patient, e.g. an aneurysm 20.

Device 310 comprises guidewire 320 coaxial to tubular portion 330.

Figure 12:
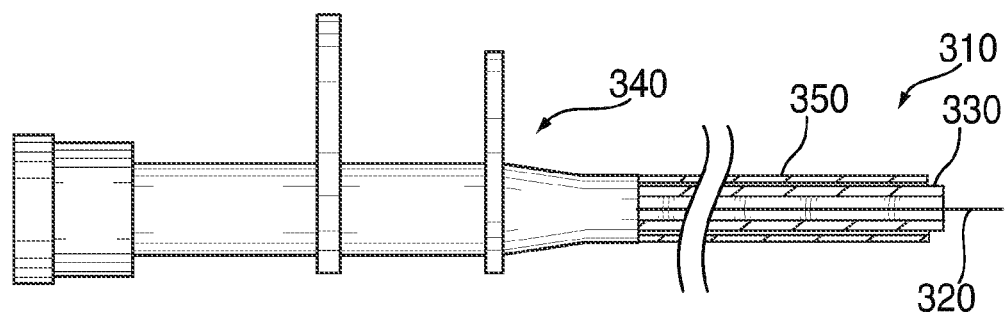
FIG. 12 is a representation of a partial cross-section of the device showing an inner member and an outer member.

FIG. 12 depicts device 310 along with an additional outer sleeve 350. In some embodiments, outer sleeve 350 functions to deploy ligature 30. Thus, in some embodiments, outer sheath 350 composes a holdfast-delivery or ligature-delivery moiety.

Figure 13:
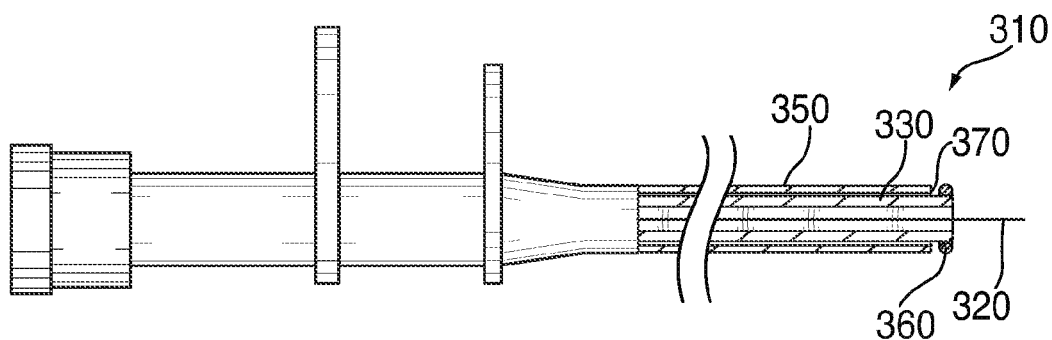
FIG. 13 is a representation of a partial cross-section of a device showing the distal end of the device and the ligature in cross-section.

FIG. 13 depicts an embodiment of device 310 with an embodiment of ligature 360 shown in cross-section. In various embodiments, ligature 360 comprises a lasso, a band, a clip, a clamp, a ferrule, a coil, a tie, an eyelet, or a clasp.

Figure 14:
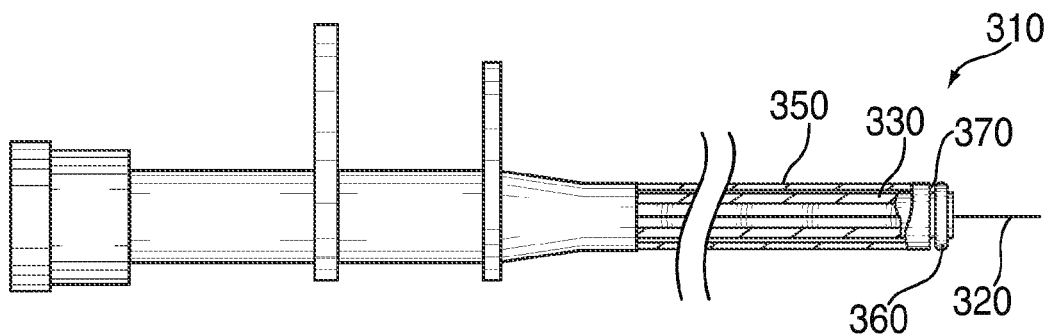
FIG. 14 is a representation of a partial cross-section of a device showing the distal end of the device in which the tip of the device and the ligature are no longer in cross-section.

FIG. 14 is similar to FIG. 13 except that the tip of the device 310 and ligature 360 are not shown in cross-section.

The device 310 can be made from typical catheter construction materials. These materials are biocompatible and are well known in the art. A non-exhaustive listing of these materials includes: nylon, urethane, polyurethane, polyvinylchloride, polyester, PEEK, PTFE, PVDF, Kyner, polyimide, or polyethylene of various suitable densities.

Various methods of ligating the tissue are useful. The tissue may be ligated with a lasso mechanism that loops around the tissue and is secured by tensioning one end of the lasso. Tensioning the end causes the movement of a slipknot, for example, that would allow the lasso to tighten but would prevent the lasso from loosening. Alternatively, the ligature 30 may be a band, such as an elastic band, to be placed around the tissue. Various biocompatible elastomeric materials may be used for this purpose.

The ligature 30, 360 may be made from a number of materials that are biocompatible and suitable for medical device implants. For example, the ligature 30, 360 may be made from materials that are traditionally used for suture products. A non-exhaustive list of suitable ligature materials would include absorbable materials such as plain catgut, chromic catgut, polyglycolic acid (PGA), and polydioxanone (PDS), for example, or non-absorbable materials such as nylon, linen, silk, polypropylene, or polyester, for example. Furthermore, in the example of an elastomeric ligature described above, the ligature could be formed from silicone or thermoplastic elastomers.

Various methods of ligating the tissue are useful. As briefly described above, the anchor material may depend on the application, but could be selected from the group of materials comprising stainless steel, silver, platinum, tantalum, palladium, cobalt-chromium alloys such as L605, MP35N, or MP20N, niobium, iridium, any equivalents thereof, alloys thereof, and combinations thereof, or nickel titanium, or poly(alpha-hydroxy esters), polylactic acids, polylactides, poly-L-lactide, poly-DL-lactide, poly-L-lactide-co-DL-lactide, polyglycolic acids, polyglycolide, poly-lactic-co-glycolic acids, polyglycolide-co-lactide, polyglycolide-co-DL-lactide, polyglycolide-co-L-lactide, polyanhydrides, polyanhydride-co-imides, polyesters, polyorthoesters, polycaprolactones, polyanhydrides, polyphosphazenes, polyester amides, polyester urethanes, polycarbonates, polytrimethylene carbonates, polyglycolide-co-trimethylene carbonates, poly(PBA-carbonates), polyfumarates, polypropylene fumarate, poly(p-dioxanone), polyhydroxyalkanoates, polyamino acids, poly-L-tyrosines, poly(beta-hydroxybutyrate), polyhydroxybutyrate-hydroxyvaleric acids, combinations thereof, chitosan, PBT, 4-hydroxybutyrate, 3-hydroxybutyrate, or PEG.

Pieces of the device that are disposed near the distal end of the device 310 have functions that depend on the particular ligating or delivery methods or on the type of aneurysm. These distal end pieces have a variety of functions such as functions giving rise to a grasping moiety. The grasping moiety functions to anchor the distal end of device 310 to the region near ostium 20. This anchoring maintains the position of the distal end while other procedure steps occur.

Alternatively, the grasping moiety is adapted to grasp tissue, such as the anomalous tissue, in order to operate on that tissue. The grasping moiety can function to grasp aneurytic tissue during the inversion action and during any steps designed to tie off the inverted tissue or steps to cut or resect the inverted tissue.

In various embodiments, the grasping moiety uses a hook-type, friction-type, vacuum-type, adhesive-type, or clamp-type action. For example, the grasping moiety may comprise one or more hooks to capture the tissue near the treatment region or to the anomalous tissue. The hook features may be barbed or unbarbed. Their length must be sufficient to puncture and retain the anomalous tissue. Thus, hooks with an eyelet diameter of about 2 mm may be sufficient. Furthermore, hooks may be fabricated from wires of different sizes and materials. For example, a hook may be fabricated from stainless steel wire having a diameter of about 0.5 mm.

Alternatively, the grasping moiety may contain ends similar to forceps with which to grasp tissue near the treatment region. Forceps structures are well known in the art, such as those used for laparoscopic procedures. In yet other embodiments, the roughness of the grasping moiety (such as serrations or toothing on the ends of the grasping moiety) may provide a manipulating function due to the friction between the serrations or teeth. Thus, another embodiment uses a grasping moiety, which unlike forceps, has only a single probe that has serrations, teeth, or surface roughness that allows the moiety to gain traction or purchase on the tissue as the moiety pushes against the tissue.

Alternatively, the device tip (not shown) may contain an adhesive region that allows it to adhere to the vessel tissue around or near ostium 25. This connection substantially stabilizes device 310 during a retraction, resection, or ligation step, or other interventional manipulation.

In some embodiments a holdfast-delivery moiety is another piece that is at the distal end of device 310. This moiety is adapted to deliver a holdfast to the aneurytic tissue. For example, the holdfast can be a ligature and following from that the holdfast delivery moiety is adapted to deliver a ligature, in some embodiments. Ligatures surround the tissue near ostium 25 and can be selected from a lasso, a band, a clip, a clamp, a ferrule, a coil, a tie, and eyelet, or a clasp among other devices.

Another piece that can be located or used at the distal end of device 310 is a resecting moiety, in some embodiments. The resecting moiety is adapted to resect or cut tissue near the distal end of the device. In some embodiments, the resecting moiety is adapted to cut tissue adjacent or proximal to the installed ligature or ligated tissue. The resecting moiety separates the anomalous tissue or a portion of the anomalous tissue from the organism before the physician removes that tissue from the organism.

A cutting surface, device, or moiety 370, also called a resecting moiety, attaches to outer sleeve 350, in some embodiments. Cutting moiety 370 can take several forms. In some embodiments, cutting moiety 370 is a sharpened region near the end of device 310. In other embodiments, cutting moiety 370 is an assembly that functions to cut or resect tissue.

Cutting moiety 370 attaches the end of device 310 in such a way that the anomalous tissue can be resected after it is ligated or retracted. Cutting moiety 370 can include a sharpened blade that extends from a catheter end. Alternatively, cutting moiety 370 may be a scissor-like, end-effector on a catheter end. In this embodiment, the scissors would substantially resemble forceps with blades in place of the jaws. Alternatively, a catheter may have end lumens that are able to suck tissue into the catheter body. Once secured, an internal cutting moiety such as a blade, grinding bur, or RF element may be advanced toward the tissue in order to cut it.

The device may benefit from commonly used medical device coatings, such as hydrophilic or hydrophobic coatings, that enable easier delivery. Furthermore, the implant itself, such as the ligature, may benefit from coatings that include non-proliferative drugs to prevent adverse tissue reactions. Other useful coatings may include drugs. Useful drugs for component coatings or for delivery before, during, or after the procedure including any drug at the physician deems useful or beneficial for the patient. Such drugs include for example, anti-inflammatory, antineoplastic, anti-platelet, anti-coagulant, coagulant, anti-fibrin, fibrin, anti-thrombotic, thrombotic, antimitotic, antibiotic, antiallergic or antioxidant compounds as desired by the physician in view of the procedure's overall goals.

In operation, device 310 is inserted into a body lumen, in some embodiments, percutaneously. For intervention with tissue located near or part of tissue of the alimentary tract or tissue located near or part of intestinal tissue, deliver of the device can be accomplished through the intestinal or alimentary tract. The user advances guidewire 320 until it is near the treatment area, such as the location of the anomalous tissue or the aneurytic tissue. Then, the device 310 tracks along guidewire 320 until the device 310 is close enough to the aneurytic tissue for operating on the tissue. The user retracts the anomalous or aneurytic tissue using inner member 330 or a grasping or holding, device or moiety attached to the distal end of inner member 330 or the distal end of device 310. The grasping moiety is adapted to hold or grasp the tissue. In the case of anomalous or aneurytic tissue outside of the body lumen, retraction includes inverting the tissue through the opening or ostium between the body lumen and the tissue.

In a slightly different configuration, vacuum or suction may be applied to one of the illustrated lumens of device 310 or device 310 may comprise a separate suction lumen (not shown). Either of these applications of vacuum or suction can act to grasp the tissue—the suction increasing the friction between the tissue and the end of device 310 to enable the tissue to be grasped or manipulated. Important factors in determining the suction force that can be applied include the size of the lumen through which suction is being drawn. The larger this lumen, the greater the suction force applied. As an example, this lumen may be in the range of about 0.010 inch to about 0.050 inch. Various vacuum sources can be used, including vacuum pumping stations and simple syringes. These vacuum sources can connect to a proximal port that is in fluid communication with the lumen. Thus, vacuum can be drawn and released through the lumen.

In some embodiments, grasping tissue with the tissue-grasping moiety creates a narrowed-down region or tissue neck. This tissue neck is the target of ligature 360, in some embodiments.

In some embodiments, after retraction, ligature 360 is delivered to ligate the tissue. Said another way, ligature 360 is delivered around the tissue to secure the tissue And after ligation of the tissue, the anomalous or aneurytic tissue is cut or resected from the body using cutting moiety 370 located or attached to the distal end of outer sleeve 350.

In addition to the disease processes described above, the devices and methods described in this document can be used to treat the following diseases or processes.

Left Atrial Appendage: Left atrial appendage refers to a muscular pouch that may exist in the left atrium of the heart. It is clinically significant because there is a risk of blood clot formation during atrial fibrillation due to the relatively stagnant volume of blood in this pouch. Therefore, there is sometimes a need for reducing the volume of the left atrial appendage. The device of this invention can be used to reduce the atrial volume by inverting the pouch and then ligating it securely closed.

Obesity Treatment: Gastric reduction is one method of treating obesity. In it a portion of the stomach is typically either resected or stapled shut. This invention could be used to perform gastric reduction by inverting a portion of the stomach and then clipping the stomach such that the overall volume is reduced.

Appendix Removal: The vermiform appendix is a vestigial organ connected to the cecum. It can become infected, which leads to the need to remove it in order to prevent harm to the patient. This removal process is called an appendectomy and is often performed endoscopically. This invention proposes the use of a device to invert the appendix until it is positioned within the intestines and then ligating the appendix closed.

Lung Volume Reduction: Lung volume reduction surgery is commonly performed on emphysema patients that have sections of their lungs with compromised function. By surgically removing the lung lobe or portion, space is freed within the chest cavity into which the healthy lung may expand. This improves overall breathing capacity. This invention may be used to invert and ligate sections of the lung with compromised capacity in order to reduce the volume of those sections and to allow healthy sections to expand for improved lung capacity.

Venous Aneurysm: Aneurysm such as those found in the arterial system can also arise in the venous system. For example, a popliteal venous aneurysm is a relatively common condition in which the vein wall distends and ultimately ruptures with the accompanying problems this can create. The device of this invention can be used to treat a venous aneurysm in the same manner as for arterial aneurysms.

Gall Bladder: The gall bladder is a non-vital organ that stores bile to aid in the digestion of fat. Occasionally, disease of the gall bladder requires its removal. Using this invention, the gall bladder may be inverted to significantly reduce its volume rather than removing it entirely.

"Adapted for percutaneous delivery" encompasses a multitude of adaptations that have taken place over decades to medical devices enabling the devices to be used to perform procedures using percutaneous routes to access animal vasculature. And these adaptations are well-known to those of ordinary skill in the art. At its simplest, "adapted for percutaneous delivery" encompasses any adaptation to a medical device to make percutaneous delivery possible or more easily accomplished. For instance, making a device small enough to traverse the vasculature or long enough to reach from the desired site of intervention out through the skin access point are both fundamental examples of adaptations for percutaneous access or delivery. Constructing a device that allows external control over the distal end pieces or tooling so that desired manipulations can be achieved is another. The choice of construction material to provide strong enough devices while minimizing undesired physical, biological, or chemical interactions between the device and the organism are likewise adaptations for percutaneous delivery. The feature that these adaptations share is a purposeful choice (not an accidental occurrence) to make an medical device more suitable for percutaneous use or delivery.

These principles relate to the meaning of "adapted for elementary or intestinal delivery", as well.

While particular embodiments of the present invention have been shown and described, it will be obvious to those skilled in the art that changes and modifications can be made without departing from the embodiments of this invention in its broader aspects and, therefore, the appended claims are to encompass within their scope all such changes and modifications as fall within the true spirit and scope of the embodiments of this invention. Additionally, various embodiments have been described above. For convenience's sake, combinations of aspects composing invention embodiments have been listed in such a way that one of ordinary skill in the art may read them exclusive of each other when they are not necessarily intended to be exclusive. But a recitation of an aspect for one embodiment is meant to disclose its use in all embodiments in which that aspect can be incorporated without undue experimentation. In like manner, a recitation of an aspect as composing part of an embodiment is a tacit recognition that a supplementary embodiment exists that specifically excludes that aspect. All patents, test procedures, and other documents cited in this specification are fully incorporated by reference to the extent that this material is consistent with this specification and for all jurisdictions in which such incorporation is permitted.

Moreover, some embodiments recite ranges. When this is done, it is meant to disclose the ranges as a range, and to disclose each and every point within the range, including end points. For those embodiments that disclose a specific value or condition for an aspect, supplementary embodiments exist that are otherwise identical, but that specifically exclude the value or the conditions for the aspect.

Finally, headings are for the convenience of the reader and do not alter the meaning or content of the disclosure or the scope of the claims.

What is claimed is:

1. A device, comprising:
   an inner catheter member having an outer surface, an inner lumen, and a distal end;
   a distal end piece mounted on the distal end, wherein the distal end piece includes a grasping moiety attached to the distal end of the inner catheter member, wherein the grasping moiety includes a tractional probe to gain traction on a tissue to stabilize the inner catheter member against the tissue;
   an outer catheter member coaxial with the inner catheter member; and
   a ligature deformed on the outer surface of the inner catheter member distal to the outer catheter member, wherein advancement of the outer catheter member deploys the ligature past the distal end of the inner catheter member.

2. The device of claim 1, wherein the ligature includes at least one of a filament, a cord, or a wire, and wherein the ligature is semi-flexible.

3. The device of claim 1, wherein the ligature includes at least one of a filament, a cord, or a wire, and wherein the ligature is elastically deformable.

4. The device of claim 3, wherein the ligature includes at least one of a silicone or a thermoplastic elastomer.

5. The device of claim 1 further comprising a plurality of anchors coupled with the ligature, wherein the plurality of anchors are configured to grasp the tissue.

6. The device of claim 5, wherein the tractional probe includes an adhesive to adhere to the tissue.

7. The device of claim 5, wherein the tractional probe is configured to grasp the tissue.

8. The device of claim 7 further comprising a resecting moiety, wherein the resecting moiety is disposed within the inner lumen and is configured to separate the grasped tissue proximal to the deployed ligature.

9. The device of claim 1, wherein the ligature includes a drug coating.

10. The device of claim 1 further comprising a handle, wherein the handle is attached to respective proximal ends of the inner catheter member and the outer catheter member, and wherein the handle is configured to advance the outer catheter member relative to the inner catheter member.

11. A method comprising:
   inserting a device percutaneously into a vasculature, wherein the device comprises:
      an inner catheter member having an outer surface, an inner lumen, and a distal end,
      a distal end piece mounted on the distal end, wherein the distal end piece includes a grasping moiety attached to the distal end of the inner catheter member, wherein the grasping moiety includes a tractional probe to gain traction on a tissue to stabilize the inner catheter member against the tissue,
      an outer catheter member coaxial with the inner catheter member, and
      a ligature deformed on the outer surface of the inner catheter member distal to the outer catheter member, wherein advancement of the outer catheter member deploys the ligature past the distal end of the inner catheter member;
   grasping, by the grasping moiety, the tissue to create a narrowed-down tissue neck; and
   deploying the ligature past the distal end of the inner tubular member to substantially encircle the narrowed-down tissue neck.

12. The method of claim 11, wherein grasping the tissue includes sucking the tissue into the inner lumen such that the tissue forms the narrowed-down tissue neck adjacent to the distal end.

13. The method of claim 11 further comprising clamping the ligature to the narrowed-down tissue neck substantially to secure the tissue.

14. The method of claim 13, wherein the clamping includes transitioning the ligature from a deformed diameter to a deployed diameter.

15. The method of claim 14, wherein the ligature is elastically deformed on the outer surface and includes one or more anchors, and wherein deploying the ligature includes anchoring the one or more anchors into the tissue encircling the narrowed-down tissue neck.

16. The method of claim 11 further comprising severing, by a resecting moiety of the device, the tissue between the ligature and the distal end.

17. The method of claim 16 further comprising removing the severed tissue from a patient.

* * * * *